(12) United States Patent
Bergeron, Jr.

(10) Patent No.: US 7,423,182 B2
(45) Date of Patent: Sep. 9, 2008

(54) AMINATED POLYAMINES

(75) Inventor: Raymond J. Bergeron, Jr., Gainesville, FL (US)

(73) Assignee: University of Florida, Gainesville, FL (US)

( * ) Notice: Subject to any disclaimer, the term of this patent is extended or adjusted under 35 U.S.C. 154(b) by 251 days.

(21) Appl. No.: 10/979,765

(22) Filed: Nov. 3, 2004

(65) Prior Publication Data

US 2006/0094791 A1    May 4, 2006

(51) Int. Cl.
*C07C 211/13* (2006.01)
*A61K 31/13* (2006.01)

(52) U.S. Cl. .................................. 564/512; 514/674
(58) Field of Classification Search .................. 564/512
See application file for complete search history.

(56) References Cited

U.S. PATENT DOCUMENTS

| 5,091,576 | A | | 2/1992 | Bergeron |
| 5,128,353 | A | | 7/1992 | Bergeron |
| 5,173,505 | A | | 12/1992 | Bergeron |
| 5,886,050 | A | | 3/1999 | Bergeron, Jr. |
| 5,962,533 | A | | 10/1999 | Bergeron, Jr. |
| 2003/0185778 | A1 | * | 10/2003 | Fahl et al. .................. 424/70.1 |

FOREIGN PATENT DOCUMENTS

WO    WO 91/00853 A    1/1991

OTHER PUBLICATIONS

Janne et al., A Biochim. Biophys. Acta., vol. 473, p. 241 (1978).
Fillingame et al., Proc. Natl. Acad. Sci. U.S.A., vol. 72, p. 4042 (1975).
Metcalf et al., J. Am. Chem. Soc., vol. 100, p. 2551 (1978).
Flink et al., Nature (London), vol. 253, p. 62 (1975).
Pegg et al., Polyamine Metabolism and Function, Am. J. Cell. Physiol., vol. 243, pp. 212-221 (1982).
Dykstra et al., Science, vol. 149, p. 428 (1965).
Russell et al., Polyamines as Biochemical Markers of Normal and Malignant Growth (Raven, New York, 1978).
Hirshfield et al., J. Bacteriol., vol. 101, p. 725 (1970).
Hafner et al., J. Biol. Chem., vol. 254, p. 12419 (1979).
Cohn et al., J. Bacteriol., vol. 134, p. 208 (1978).
Pohjanpelto et al., Nature (London), vol. 293, p. 475 (1981).
Mamont et al., Biochem. Biophys. Res. Commun., vol. 81, p. 58 (1978).
Bloomfield et al., "Polyamines in Biology and Medicine", D.R. Morris and L.J. Morton, eds., Dekker, New York, pp. 183-206 (1981).
Gosule et al., Nature, vol. 259, p. 333 (1976).
Gabbay et al., Ann. N.Y. Acad. Sci., vol. 171, p. 810 (1970).
Suwalsky et al., J.Mol. Biol., vol. 42, p. 363 (1969).
Liquori et al., J. Mol. Biol., vol. 24, p. 113 (1967).
Sjoerdsma et al., Butterworths Int. Med. Rev.: Clin. Pharmacol. Thera., vol. 35, p. 287 (1984).
Israel et al., J. Med. Chem., vol. 16, p. 1 (1973).

Morris et al., Polyamines in Biology and Medicine, Dekker, New York, p. 223 (1981).
Wang et al., Biochem. Biophys. Res. Commun., vol. 94, p. 85 (1980).
Bergeron et al., "The role of methylene backbone in the anti-proliferative activity of polyamine analogues on L1210 cells", Cancer Res., vol. 49, pp. 2959-2964 (1989).
Bergeron et al., "Synthetic polyamine analogues as antineoplastics", J. Med. Chem., vol. 31, pp. 1183-1190 (1988).
Porter et al., "Regulation of polyamine biosynthetic activity by spermidine and spermine— a novel antiproliferative strategy", Polyamines in Biochemical and Clinical Research, pp. 677-690 (1988).
Libby et al., "Major increases in spermidine/spernine-N.sup.1-acetyl transferase activity by spermine analogues and their relationship to polyamine depletion and growth inhibition in L1210 cells", Cancer Res., vol. 49, pp. 6226-6231 (1989).
Pegg et al., "Induction of spermidine/spermine N.sup.1 -acetyl transferase activity in Chinese-hamster ovary cells by N.sup.1,N.sup.1,N.sup.11 -bis(ethyl)norspennine and related compounds", Biochem. J., vol. 267, pp. 331-338 (1990).
Porter et al., "Combined regulation of ornithine and S-adenosylmethionine decarboxylases by spermine and the spermine analogue N.sup.1 N.sup.12 -bis(ethyl)spermine", Biochem. J., vol. 268, pp. 207-212 (1990).
Basu et al., "Effect of N.sup.1,N.sup.14 -bis(ethyl)-homospermine on the growth of U-87 MG and SF-126 on human brain tumor cells", Cancer Res., vol. 50, pp. 3137-3140 (1990).
Stewart, "The effects of structural changes in a polyamine backbone on its DNA binding properties", Biochem. Biophys. Res. Commun., vol. 152, pp. 1441-1446 (1988).

(Continued)

*Primary Examiner*—Brian J Davis
(74) *Attorney, Agent, or Firm*—Miles & Stockbridge P.C.

(57) ABSTRACT

An aminated polyamine having the formula:

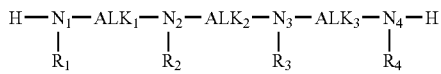

or its possible stereoisomers or a salt thereof with a pharmaceutically acceptable acid wherein:

$R_1$ and $R_4$ may be the same or different and are alkyl, aryl, aryl alkyl or cycloalkyl, optionally having an alkyl chain interrupted by at least one etheric oxygen atom;

$R_2$ and $R_3$ may be the same or different and are $R_1$, $R_4$ or H;

$N_1$, $N_2$, $N_3$ and $N_4$ are nitrogen atoms capable of protonation at physiological pH's;

$ALK_1$, $ALK_2$ AND $ALK_3$ may be the same or different and are straight or branched chain alkylene bridging groups having 1 to 4 carbon atoms which effectively maintain a predetermined distance between the nitrogen atoms such that the polyamine upon uptake by the target cell, competitively functions in a manner wherein at least one of said bridging groups $ALK_1$, $ALK_2$ and $ALK_3$ contains at least one —CH(NRH)— group which is not alpha- to either of the nitrogen atoms and R is H, alkyl, acyl or sulfonyl.

10 Claims, 1 Drawing Sheet

OTHER PUBLICATIONS

Bergeron et al., "Synthesis of $N^4$-acylated $N^1,N^8$-bis(acyl)spermidines: An approach to the synthesis of siderophores", J. Org. Chem., vol. 45, pp. 1589-1592 (1980).

Bergeron et al., "Reagents for the selective acylation of spermidine, homospermidine and bis-> 3-aminopropylamine", Synthesis, pp. 732-733 (1981).

Bergeron et al., "Reagents for the selective secondary functionalization of linear triamines", Synthesis, pp. 689-692 (1982).

Bergeron et al., "Amines and polyamines from nitriles", Synthesis, pp. 782-785 (1984).

Bergeron et al., "Reagents for the stepwise functionalization of spermidine, homospermidine and bis->3-aminopropylamine", J. Org. Chem., vol. 49, p. 2997 (1984).

Bergeron, "Methods for the selective modification of spermidine and its homologues", Accts. Chem. Res., vol. 19, pp. 105-113 (1986).

Bergeron et al., "Hexahydropyrimidines as masked spermidine vectors in drug delivery", Bioorg. Chem., vol. 14, pp. 345-355 (1986).

Bergeron et al., "Reagents for the stepwise functionalization of spermine", J. Org. Chem., vol. 53, pp. 3108-3111 (1988).

Bergeron et al., "Total synthesis of (.+-.)-15-Deoxyspergualin", J. Org. Chem., vol. 52, pp. 1700-1703 (1987).

Bergeron et al., "The total synthesis of Alealigin", J. Org. Chem., vol. 56, pp. 586-593 (1991).

Bergeron et al. "Synthesis of catecholamide and hydroxamate siderophores", CRC Handbook on Microbial Iron Chelates, pp. 271-307 (1991).

Porter et al., "A comparison and characterization of growth inhibition by .alpha.-Difluoromethylomithine (DFMO), and inhibitor of omithine decarboxylase and $N^1,N^8$-bis(ethyl)spermidine (BES), and apparent regulator of the enzyme", Cancer Res., vol. 46, pp. 6279-6285 (1986).

Porter et al., "Relative abilities of bis(ethyl) derivatives of putrescine, spermidine and spermine to regulate polyamine biosynthesis and inhibit L1210 leukemia cell growth", Cancer Res., vol. 47, pp. 2821-2825 (1987).

Basu et al., "Correlation between the effects of polyamine analogues on DNA conformation and cell growth", Cancer Res., vol. 49, pp. 5591-5597 (1989).

Casero et al., "Differential response to treatment with the bis(ethyl)polyamine analogues between human small cell lung carcinoma and undifferentiated large cell lung carcinoma in culture", Cancer Res., vol. 49, pp. 639-643 (1988).

Vertino et al., "Selective cellular depletion of mitochondrial DNA by the polyamine analog. $N^1,N^{12}$—bis(ethyl)spermine, and its relationship to polyamine structure and function", Mol. Pharm., vol. 39, pp. 487-494 (1991).

Chang et al., "Modulation of polyamine biosynthesis and transport by oncogene transfection", Biochem. and Biophys. Res. Commun., vol. 157, pp. 264-270 (1988).

Vertino et al., "Structural determinants of spermidine-DNA interactions", Biopolymers, vol. 26, pp. 691-703 (1987).

Bergeron et al., "Antiproliferative Properties of Polyamine Analogues: A Structure-Activity Study", J. Med. Chem. vol. 37, pp. 3464-3476 (1994).

Bergeron et al., "The Role of Charge in Polyamine Analogue Recognition", J. Med. Chem., vol. 38, pp. 2278-2285 (1995).

Bergeron et al., J. Med. Chem., vol. 46, pp. 5478-5483 (2003).

Communication dated May 15, 2008 in EP 04 80 0606 transmitting Supplementary Partial European Search Report.

Bergeron, Raymond J. et al.: "Synthetic Polyamine Analogs as Antineoplastics" Journal of Medicinal Chemistry, 31 (6), 1183-90 Coden; JMCMAR; ISSN 0022-2623, 1998, XP002291373. *the entire document*

* cited by examiner

AMINATED POLYAMINES

BACKGROUND OF THE INVENTION

1. Field of the Invention

The invention relates to novel aminated polyamines having valuable therapeutic and other biological properties.

2. Discussion of the Prior Art

In recent years, a great deal of attention has been focused on the polyamines, e.g., spermidine, norspermidine, homospermidine, 1,4-diaminobutane (putrescine) and spermine. These studies have been largely directed at the biological properties of the polyamines probably because of the role they play in proliferative processes. It was shown early on that the polyamine levels in dividing cells, e.g., cancer cells, are much higher than in resting cells. See Janne et al, A. Biochim. Biophys. Acta., Vol. 473, page 241 (1978); Fillingame et al, Proc. Natl. Acad. Sci. U.S.A., Vol. 72, page 4042 (1975); Metcalf et al, J. Am. Chem. Soc., Vol. 100, page 2551 (1978); Flink et al, Nature (London), Vol. 253, page 62 (1975); and Pegg et al, Polyamine Metabolism and Function, Am. J. Cell. Physiol., Vol. 243, pages 212-221 (1982).

Several lines of evidence indicate that polyamines, particularly spermidine, are required for cell proliferation: (i) they are found in greater amounts in growing than in non-growing tissues; (ii) prokaryotic and eukaryotic mutants deficient in polyamine biosynthesis are auxotrophic for polyamines; and (iii) inhibitors specific for polyamine biosynthesis also inhibit cell growth. Despite this evidence, the precise biological role of polyamines in cell proliferation is uncertain. It has been suggested that polyamines, by virtue of their charged nature under physiological conditions and their conformational flexibility, might serve to stabilize macromolecules such as nucleic acids by anion neutralization. See Dkystra et al, Science, Vol. 149, page 48 (1965); Russell et al, Polyamines as Biochemical Markers of Normal and Malignant Growth (Raven, N.Y., 1978); Hirschfield et al, J. Bacteriol., Vol. 101, page 725 (1970); Hafner et al, J. Biol. Chem., Vol. 254, page 12419 (1979); Cohn et al, J. Bacteriol., Vol. 134, page 208 (1978); Pohjatipelto et al, Nature (London), Vol. 293, page 475 (1981); Mamont et al, Biochem. Biophys. Res. Commun., Vol. 81, page 58 (1978); Bloomfield et al, Polyamines in Biology and Medicine (D. R. Morris and L. J. Morton, eds., Dekker, New York, 1981), pages 183-205; Gosule et al, Nature, Vol. 259, page 333 (1976); Gabbay et al, Ann. N.Y. Acad. Sci., Vol. 171, page 810 (1970); Suwalsky et al, J. Mol. Biol., Vol. 42, page 363 (1969); and Liquori et al, J. Mol. Biol., Vol. 24, page 113 (1968).

However, regardless of the reason for increased polyamine levels, the phenomenon can be and has been exploited in chemotherapy. See Sjoerdsma et al, Buttenvorths Int. Med. Rev.: Clin. Pharmacol. Thera., Vol. 35, page 287 (1984); Israel et al, J. Med. Chem., Vol. 16, page 1 (1973); Morris et al, Polyamines in Biology and Medicine, Dekker, New York, page 223 (1981); and Wang et al, Biochem. Biophys. Res. Commun., Vol. 94, page 85 (1980).

Because of the role the natural polyamines play in proliferation, a great deal of effort has been invested in the development of polyamine analogues as antiproliferatives>Cancer Res., Vol. 49, "The role of methylene backbone in the anti-proliferative activity of polyamine analogues on L1210 cells," Bergeron et al, pages 2959-2964 (1989); J. Med. Chem., Vol. 31, "Synthetic polyamine analogues as antineoplastics," Bergeron et al, pages 1183-1190 (1988); Polyamines in Biochemical and Clinical Research, "Regulation of polyamine biosynthetic activity by spermidine and spermine—a novel antiproliferative strategy," Porter et al, pages 677-690 (1988); Cancer Res., Vol. 49, "Major increases in spermidine/spermine-$N^1$-acetyl transferase activity by spermine analogues and their relationship to polyamine depletion and growth inhibition in L1210 cells," Basu et al, pages 6226-6231 (1989); Biochem. J., Vol. 267, "Induction of spermidine/spermine $N^1$-acetyl transferase activity in Chinese-hamster ovary cells by $N^1,N^{11}$-bis(ethyl)norspermine and related compounds," Pegg et al, pages 331-338 (1990); Biochem. J., Vol. 268, "Combined regulation of ornithine and S-adenosylmethionine decarboxylases by spermine and the spermine analogue $N^1$ $N^{12}$-bis(ethyl)spermine," Porter et al, pages 207-212 (1990); Cancer Res., Vol. 50, "Effect of $N^1,N^{14}$-bis(ethyl)-homospermine on the growth of U-87 MG and SF-126 on human brain tumor cells," Basu et al, pages 3137-3140 (1990); and Biochem. Biophys. Res. Commun., Vol. 152, "The effect of structural changes in a polyamine backbone on its DNA binding properties," Stewart, pages 1441-1446 (1988)!. These efforts have included the design of new synthetic methods>J. Org. Chem., Vol. 45, "Synthesis of $N^4$-acylated $N^1,N^8$-bis(acyl) spermidines: An approach to the synthesis of siderophores," Bergeron et al, pages 1589-1592 (1980); Synthesis, "Reagents for the selective acylation of spermidine, homospermidine and bis->3-aminopropyl!amine," Bergeron et al, pages 732-733 (1981); Synthesis, "Reagents for the selective secondary functionalization of linear triamines," Bergeron et al, pages 689-692 (1982); Synthesis, "Amines and polyamines from nitriles," Bergeron et al, pages 782-785 (1984); J. Org. Chem., Vol. 49, "Reagents for the stepwise functionalization of spermidine, homospermidine and bis->3-aminopropyl!amine," Bergeron et al, page 2997 (1984); Accts. Chem. Res., Vol. 19, "Methods for the selective modification of spermidine and its homologues," Bergeron, pages 105-113 (1986); Bioorg. Chem., Vol. 14, "Hexahydropyrimidines as masked spermidine vectors in drug delivery," Bergeron et al, pages 345-355 (1986); J. Org. Chem., Vol. 53, "Reagents for the stepwise functionalization of spermine," Bergeron et al, pages 3108-3111 (1988); J. Org. Chem., Vol. 52, "Total synthesis of (.+-.)-15-Deoxyspergualin," Bergeron et al, pages 1700-1703 (1987); J. Org. Chem., Vol. 56, "The total synthesis of Alcaligin," Bergeron et al, pages 586-593 (1991); and CRC Handbook on Microbial Iron Chelates, "Synthesis of catecholamide and hydroxamate siderophores," Bergeron et al, pages 271-307 (1991)! for the production of these analogues, as well as extensive biochemical studies focused on the mechanism by which these compounds act>Cancer Res., Vol. 46, "A comparison and characterization of growth inhibition by .alpha.-Difluoromethylomithine (DFMO), and inhibitor of ornithine decarboxylase and $N^1,N^8$-bis(ethyl)spermidine (BES), an apparent regulator of the enzyme," Porter et al, pages 6279-6285 (1986); Cancer Res., Vol. 47, "Relative abilities of bis(ethyl) derivatives of putrescine, spermidine and spermine to regulate polyamine biosynthesis and inhibit L1210 leukemia cell growth," Porter et al, pages 2821-2825 (1987); Cancer Res., Vol. 49, "Correlation between the effects of polyamine analogues on DNA conformation and cell growth," Basu et al, pages 5591-5597 (1989); Cancer Res., Vol. 49, "Differential response to treatment with the bis(ethyl)polyamine analogues between human small cell lung carcinoma and undifferentiated large cell lung carcinoma in culture," Casero et al, pages 639-643 (1988); Mol. Pharm., Vol. 39, "Selective cellular depletion of mitochondrial DNA by the polyamine analog, $N^1,N^{12}$-bis(ethyl)spermine, and its relationship to polyamine structure and function," Vertino et al, pages 487-494 (1991); Biochem. and Biophys. Res. Comm., Vol. 157, "Modulation of polyamine biosynthesis and transport by oncogene transfection," Chang et al, pages 264-270 (1988); and Biopolymers, Vol. 26, "Structural determinants of spermidine-DNA interactions," Vertino et al, pages 691-703 (1987)!. The mechanistic investigations have encompassed uptake studies, impact on polyamine analogues on polyamine pools and polyamine biosynthetic enzymes, as well as their effects on translational and transcriptional events.

Anti-neoplastic analogues of the naturally occurring polyamines, pharmaceutical compositions and methods of treatment are also disclosed in the following pending patent application Ser. No. 08/231,692 filed Apr. 25, 1994, as well as in U.S. Pat. No. 5,091,576 issued Feb. 25, 1992; U.S. Pat. No. 5,128,353 issued Jul. 7, 1992; U.S. Pat. No. 5,173,505 issued Dec. 22, 1992 and U.S. Pat. No. 5,962,533, issued Oct. 5, 1999. The disclosures of each of the foregoing applications and patents are incorporated herein by reference.

Many of the biologically and pharmacologically valuable polyamines, however, present troublesome metabolic properties in that they are metabolized after administration to the whole animal to potentially toxic metabolites, several of which have a protracted half-life in animals.

Diethylnorspermine (DENSPM) and its metabolites are found in all of the tissues of mice treated with the drug, with the liver and kidney having the highest level of metabolites. These catabolic products included N.sup.1-ethylnorspermine (MENSPM), N.sup.1-ethylnorspermidine (MENSPD), N.sup.1-ethyl-1,3-diaminopropane (MEDAP) and norspermidine (NSPD), suggesting that DENSPM is metabolized (FIG. 1) by (1) N-deethylation and (2) stepwise removal of 3-aminopropyl equivalents by spermine/spermidine N.sup.1-acetyl transferase (SSAT)/polyamine oxidase (PAO).

Diethylhomospermine is an example of a polyamine recently found to have potent activity as an anti-neoplastic and anti-diarrheal agent. Its metabolic profile indicates the highest concentration of the polyamine and its principal metabolites, N.sup.1-ethylhomospermine (MEHSPM) and homospermine (HSPM), in the liver and kidney. N-deethylation is a key metabolic step in processing DEHSPM (see FIG. 2); however, HSPM does not undergo further metabolism. The accumulation and persistence of HSPM in the tissues of DEHSPM-treated animals is especially striking. Even three weeks after a seven day schedule of DEHSPM, 35% of the drug administered to mice remains in the liver and kidney as drug or metabolites. Interestingly, 90% of the drug remaining in the animal at this time is in the form of HSPM. It is quite clear that the increased chronic toxicity of DEHSPM over N.sup.1,N.sup.4-diethylnorspermine (DENSPM) is related to the buildup of HSPM.

The key to a less toxic DEHSPM-like therapeutic agent is one in which the metabolites can be quickly cleared from the tissues. Again, because of the aminobutyl fragments of HSPM, this metabolite cannot be processed through the polyamine biosynthetic network; thus, it remains in the tissues for protracted periods of time. Neither the primary nor the secondary nitrogens of HSPM offer an opportunity for facile conversion to an easily cleared metabolite. Certainly, the methylene backbones cannot be easily oxidized to an excretable metabolite.

It is an object of the present invention to provide novel derivatives of therapeutically and biologically active polyamines which are metabolized to products quickly and easily cleared from animal tissues.

It is another object of the invention to provide novel pharmaceutical compositions and methods of treating human and non-human animals with the novel polyamine derivatives.

SUMMARY OF THE INVENTION

The above and other objects are realized by the present invention, one embodiment of which comprises aminated polyamines having the formula:

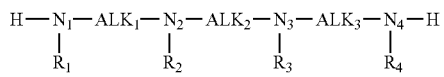

or its possible stereoisomers or salts thereof with pharmaceutically acceptable acids wherein:

$R_1$ and $R_4$ may be the same or different and are alkyl, aryl, aryl alkyl or cycloalkyl, optionally having an alkyl chain interrupted by at least one etheric oxygen atom;

$R_2$ and $R_3$ may be the same or different and are $R_1$, $R_4$ or H;

$N_1$, $N_2$, $N_3$ and $N_4$ are nitrogen atoms capable of protonation at physiological pH's;

$ALK_1$, $ALK_2$ AND $ALK_3$ may be the same or different and are straight or branched chain alkylene bridging groups having 1 to 4 carbon atoms which effectively maintain the distance between the nitrogen atoms such that the polyamine:

(i) is capable of uptake by a target cell upon administration of the polyamine to a human or non-human animal or is capable of binding to at least one polyamine site of a receptor located within or on the surface of a cell upon administration of the polyamine to a human or non-human animal; and (ii) upon uptake by the target cell, competitively binds via an electrostatic interaction between the positively charged nitrogen atoms to biological counter-anions;

the polyamine, upon binding to the biological counter-anion in the cell, functions in a manner biologically different than the intracellular polyamines; and further wherein at least one of said bridging groups $ALK_1$, $ALK_2$ and $ALK_3$ contains at least one —CH(NRH)— group which is not alpha- to either of the nitrogen atoms and R is H, alkyl, acyl or sulfonyl.

In the present invention, polyamines with asymmetric centers may occur as racemates, racemic mixtures and as individual enantiomers or diastereoisomers, with all isomeric forms of the compounds being included in the present invention.

An additional embodiment of the invention relates to compositions comprising therapeutically effective amounts of polyamines of the above formula and suitable carriers therefor.

A further embodiment of the invention concerns methods of exerting therapeutic actions on human or non-human animals requiring such action comprising administering thereto therapeutically effective amounts of polyamines of the above formula.

Another embodiment of the invention concerns the use of the aminated polyamines of the invention to serve as vectors for the introduction of pharmacores into eukaryotes and prokaryotes.

DETAILED DESCRIPTION OF THE INVENTION

Figure 1:
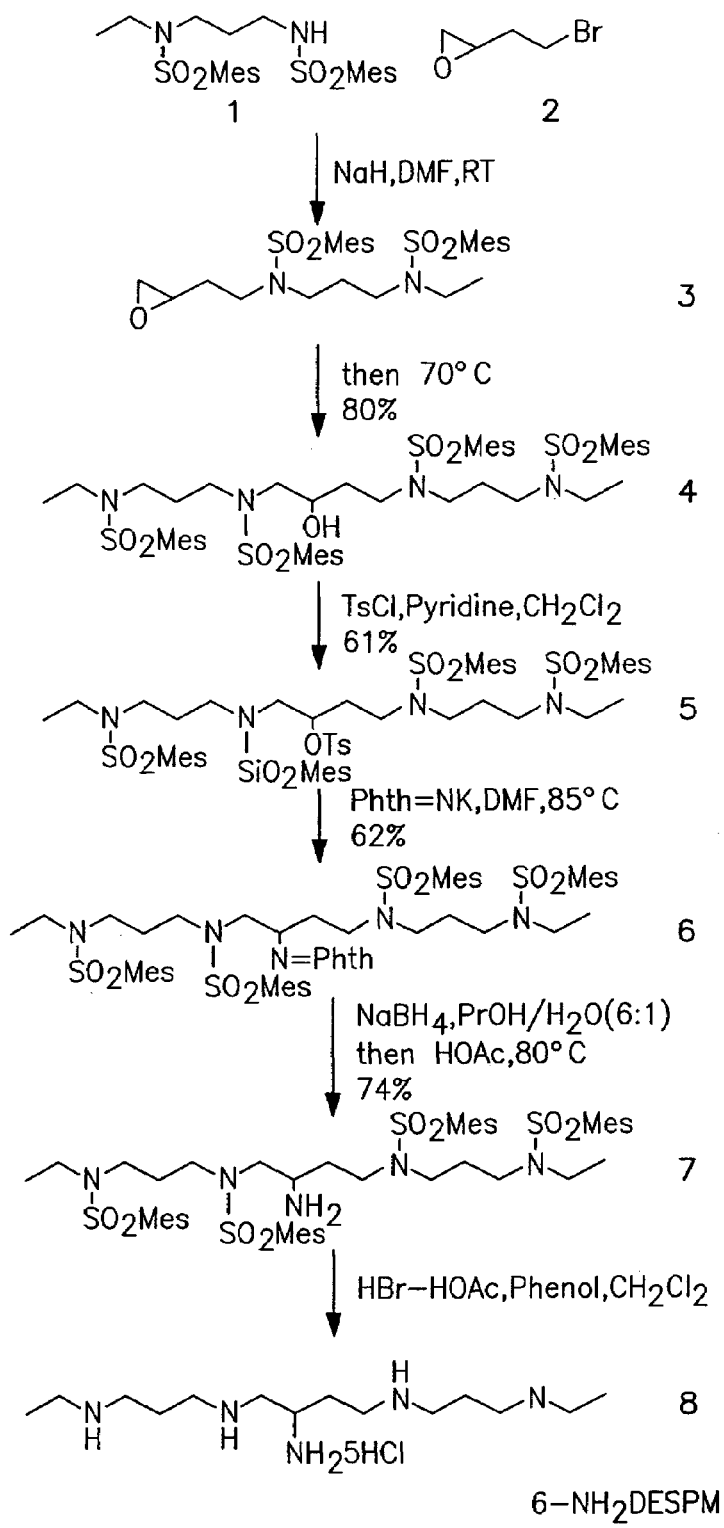
FIG. 1 depicts a reaction scheme for preparing the aminated polyamines of the invention.

As shown in the reaction scheme in FIG. 1, a novel synthetic route was developed for 6 amino-$N^1,N^{12}$-diethylspermine (6-$NH_2$ DESPM). Predominantly at room temperature, the protected diamine fragment 1 and 4-bromo-1,2-epoxybutane 2 underwent reaction to give the aminated epoxy butane 3; the ring-opening product 4 was subsequently generated in 80% yield at 70° C. The secondary hydroxyl group was tosylated (5) and then converted into phthalimide 6, followed by releasing the amino group at C-6 with sodium. borohydride to result in the primary amine 7. Finally, the deprotection of the four secondary amines furnished the desired 6-$NH_2$DESPM.

This new method is very useful for the synthesis of hydroxylated or aminated polyamines. The multifunctional 4-bromo-1,2-epoxybutane, both enantiomers of which are easy to obtain, can undergo stepwise reactions at both the brominated carbon and the terminal carbon of the epoxide; thus, it is possible to use this method for the synthesis of unsymmetric polyamines at the two sides of the butane backbone. The successful transformation of the hydroxyl group to the amino group through the Gabriel synthesis makes it possible that many of the hydroxylated polyamines disclosed in U.S. Pat. No. 5,962,533 can be converted into the corresponding aminated analogues by this method.

Polyamines of the present invention can possess one or more asymmetric carbon atoms and are thus capable of existing in the form of optical isomers, as well as in the form of racemic or non-racemic mixtures thereof. The optical isomers can be obtained by resolution of the racemic mixtures according to processes known to those skilled in the art, for example, by formation of diastereoisomeric salts by treatment with an optically active acid or base. Examples of appropriate acids are tartaric, diacetyltartaric, dibenzoyltartaric, ditoluoyltartaric and camphorsulfonic acid and the like, followed by separation of the mixture of diastereoisomers by crystallization, then release of the optically active bases from these salts.

Another example of a process for separation of optical isomers involves the use of a chiral chromatography column optimally chosen to maximize the separation of the enantiomers. The optically active compounds of the present invention can also be obtained by utilizing optically active starting materials.

Biological Studies $IC_{50}$ Studies. Although 6-$NH_2$DESPM is indeed somewhat more highly substituted than DESPM, it nevertheless maintains enough structural similarity to be "read" by L1210 cells as DESPM.

TABLE 1

L1210 Cell Growth Inhibition and Transport for Alkylated Spermine Analogues

| compound structure/abbreviation | $IC_{50}$ ($\mu M$)[a] 48 h | 96 h | $K_i$ ($\mu M$)[b] |
|---|---|---|---|
| 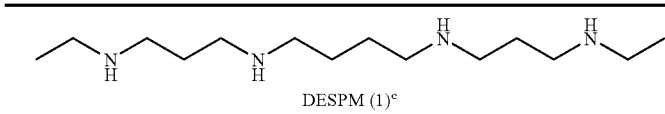 DESPM (1)[c] | 30 | 0.2 | 1.6 |
| 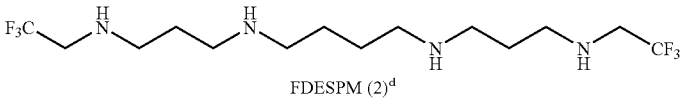 FDESPM (2)[d] | — | >100 | 285 |
| 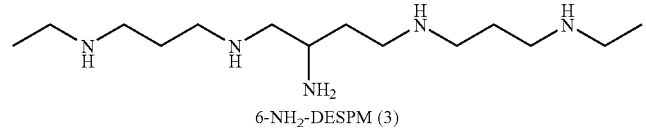 6-$NH_2$-DESPM (3) | 8 | 0.4 | 33.7 |

[a]The $IC_{50}$ was estimated from growth curves for L1210 cells grown in the presence of nine different extracellular concentrations of drug spanning four logarithmic units: 0, 0.03, 0.1, 0.3, 1.0, 3, 10, 30, and 100 $\mu M$. $IC_{50}$ data are presented as the mean of at least two experiments with variation from the mean typically 10–25% for the 96-h $IC_{50}$ values.
[b]$K_i$ determinations were made by following analogue inhibition of spermidine transport. All polyamine analogues exhibited simple substrate-competitive inhibition of [$^3$H]SPD transport by L1210 cells. Values reported in the table represent the mean of at least two or three experiments with a variation typically less than 10%.
[c]Reproduced from reference 1.
[d]Reproduced from reference 2.

TABLE 2

Effect of Alkylated Spermine Analogues on Polyamine Pools in L1210 Cells

| compd | treatment ($\mu M$) | concn PUT[a] | SPD[a] | SPM[a] | analogue[b] |
|---|---|---|---|---|---|
| DESPM[c] | 30 | 0 | 0 | 12 | 0.4 |
|  | 150 | 0 | 0 | 14 | 1.13 |
| FDESPM[d] | 100 | 100 | 103 | 108 | <0.02 |
| 6-$NH_2$-DESPM | 10 | 39 ± 9 | 16 ± 3 | 54 ± 11 | 3.52 ± 0.73 |
|  | 50 | 26 ± 1 | 7 ± 0 | 32 ± 1 | 3.10 ± 0.12 |

[a]Putrescine (PUT), spermidine (SPD), and spermine (SPM) levels after 48 h of treatment are given as percent of the polyamine found in untreated controls. The control values in pmol/$10^6$ L1210 cells are PUT = 183 ± 15, SPD = 2694 ± 232, SPM = 774 ± 81.
[b]Analogue amount is expressed as nmol/$10^6$ cells. Untreated L1210 cells ($10^6$) correspond to about 1 $\mu L$ volume; therefore, the concentration can be estimated as mM.
[c]Reproduced from reference 1.
[d]Reproduced from reference 2.

TABLE 3

Impact of Alkylated Spermine Analogues on Ornithine Decarboxylase (ODC), S-Adenosylmethionine Decarboxylase (AdoMetDC), and Spermidine/Spermine $N^1$-Acetyltransferase (SSAT) in L1210 Cells[a]

| compound | ODC | AdoMetDC | SSAT |
|---|---|---|---|
| DESPM[b] | 3 | 28 | 460 |
| FDESPM[c] | 100 | 100 | 97 |
| 6-NH$_2$-DESPM | 19 | 53 | 668 |

[a]Enzyme activity is expressed as percent of untreated control for ODC (1 □M at 4 h), AdoMetDC (1 □M at 6 h), and SSAT (10 □M at 48 h). Each experiment included a positive control which had a known, reproducible impact on enzyme activities (mean ± SD): 1 □M DEHSPM lowered ODC to 6.7 ± 2.6% of the untreated control; 1 □M DEHSPM decreased AdoMetDC to 40.7 ± 6.2% of the untreated control; and 2 □M DENSPM increased SSAT to 3877 ± 76% of the untreated control. Data shown in the table represent the mean of at least three experiments and have variances consistent with those suggested by the positive control data presented above.
[b]Reproduced from reference 1.
[c]Reproduced from reference 2.

REFERENCES (1) Bergeron, R. J.; McManis, J. S.; Liu, C. Z.; Feng, Y.; Weimar, W. R.; Luchetta, G. R.; Wu, Q.; Ortiz-Ocasio, J.; Vinson, J. R. T.; Kramer, D.; Porter, C. Antiproliferative Properties of Polyamine Analogues: A Structure-Activity Study. *J. Med. Chem.* 1994, 37, 3464-3476.

(2) Bergeron, R. J.; McManis, J. S.; Weimar, W. R.; Schreier, K. M.; Gao, F.; Wu, Q.; Ortiz-Ocasio, J.; Luchetta, G. R.; Porter, C.; Vinson, J. R. T. The Role of Charge in Polyamine Analogue Recognition. *J. Med. Chem.* 1995, 38, 2278-2285.

Description of $K_i$ Studies:

Uptake Determinations:

The polyamine derivatives were studied for their ability to compete with [$^3$H]SPD or [$^{14}$C]SPD for uptake into L1210 leukemia cells in vitro (Bergeron, R. J.; Hawthorne, T. R.; Vinson, J. R. T.; Beck, D. E., Jr.; Ingeno, M. J. Role of the Methylene Backbone in the Antiproliferative Activity of Polyamine Analogues on L1210 Cells. *Cancer Res.* 1989, 49, 2959-2964). Cell suspensions were incubated in 1 mL of RPMI-1640 containing 1, 2, 4, 6, 8, and 10 □M radiolabeled SPD alone or with the additional presence of 10, 25, and 50 □M polyamine analogue for 20 min at 37° C. At the end of the incubation period, tubes were centrifuged at 900 g for 5 min at 0-4° C. The pellet was washed twice with 5 mL of cold RPMI-1640 containing 1 □M SPD, dissolved in 200 □L of 1 N NaOH at 60° C. for 1 h, and neutralized with 1 N HCl. The material was transferred to a vial for scintillation counting. Lineweaver-Burke plots indicated a simple competitive inhibition with respect to SPD.

Another valuable embodiment of the invention comprises the value of the aminated polyamines as potential vectors for the intracellular delivery of a pharmacore wherein the vector comprises a conjugate of a polyamine covalently attached, optionally indirectly attached via a linking group, to a pharmacore, the conjugate having a polyamine moiety, wherein the polyamine moiety comprises an aminated polyamine of the invention. Preferably, the point of attachment of the pharmacore to the polyamine is at one of the —CH(RNH)— groups of either ALK1, ALK2, or ALK3.

Suitable pharmacores for conjugation with the aminated polyamines of the invention include antibiotics, antivirals or chelating agents such as the following:

L=Link to Aminopolyamine

Antibiotics

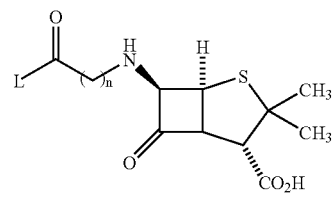

n = 1-8

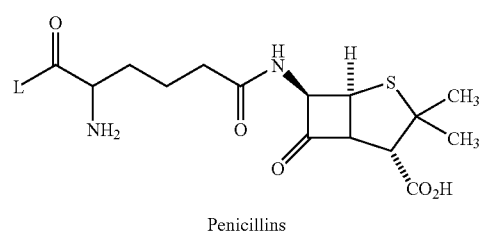

Penicillins

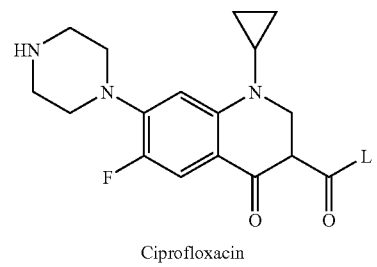

Ciprofloxacin

Antivirals

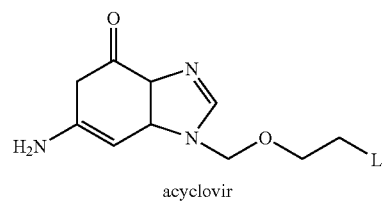

acyclovir

Chelating Agents

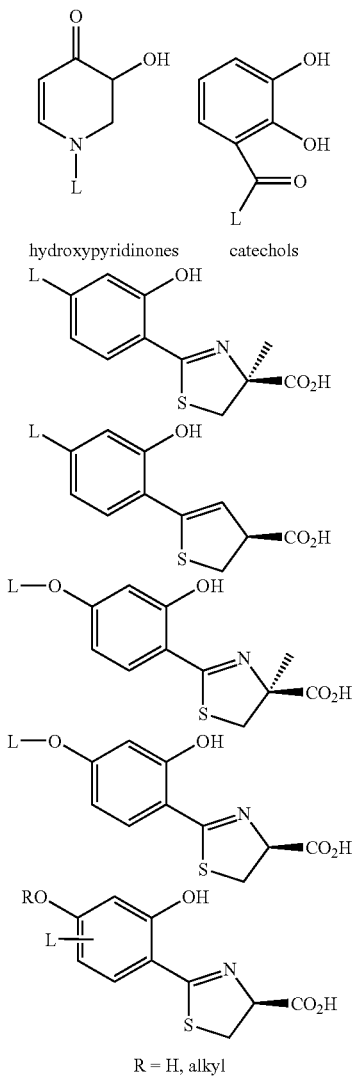

Desferrithiocin Analogues

The aminated polyamines may be conjugated with the pharmacores according to the methods described in Bergeron et al, J. Med. Chem. 2003, 46, 5478-5483 and U.S. provisional patent application Ser. No. 60/501,341, filed Sep. 9, 2003.

The articles of manufacture, method and composition of the present invention are predicated on administering to a subject (human or animal) an effective amount of one or more of the compounds described herein as being effective for the desired purpose. Administration may be accomplished either therapeutically or prophylactically by means of pharmaceutical compositions which are prepared by techniques well known in the pharmaceutical sciences. The polyamines of the present invention may be used either solely or jointly in pharmaceutically effective amounts for treating animals or humans. The polyamines of the invention can be used either solely or jointly together in pharmaceutically acceptable amounts with pharmaceutically effective amounts of other pharmaceutically active components in pharmaceutical compositions or preparations.

While the compounds of the invention are preferably administered orally, they may also be administered by a variety of other routes such as transdermally, subcutaneously, intranasally, intrarectally, intramuscularly and intravenously. The present invention is also directed to pharmaceutical compositions which include at least one compound as described above in association with one or more pharmaceutically acceptable diluents, excipients or carriers therefor. In making the pharmaceutical compositions of the present invention, one or more compounds will usually be mixed with, diluted by or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 60% by weight of active compound, soft and hard gelatin capsules, suppositories, sterile injectable solutions and sterile packaged powders. In the case of injections, it is possible to prepare solutions or suspensions of one or more polyamines of the present invention in pharmaceutically acceptable carriers such as an aqueous or nonaqueous solvent. Examples of solvents which may be used are distilled water for injection, physiological saline solution, Ringer's solution, plant oil, synthetic fatty acid glycerides, higher fatty acid esters, propylene glycol, etc.

Some examples of suitable carriers, excipients and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide rapid, sustained or delayed release of the active ingredient after administration to the patient by employing procedures well known in the art.

The dose of the compound is that amount effective for the desired purpose. By "effective amount," "therapeutic amount" or "effective dose" is meant that amount sufficient to elicit the desired pharmacological or therapeutic effects, thus resulting in effective treatment.

The effective dose may vary, depending upon factors such as the condition of the patient, the severity of the symptoms of the condition under treatment and the manner in which the pharmaceutical composition is administered. The compositions are formulated, preferably in a unit dosage form, such that each dosage contains from about 0.006 to about 12,000 mg., more usually about 0.06 to about 6,000 mg., of the active ingredient. The term "unit dosage form" refers to physically discrete units suitable as unitary dosages for human subjects and other mammals, each unit containing a predetermined quantity of active material calculated to produce the desired therapeutic effect, in association with one or more of the above-described suitable pharmaceutical diluents, excipients or carriers.

The compounds are effective over a wide dosage range in treating pain. Thus, as used herein, the term "effective amount" refers to a dosage range of from about 0.006 to about 500 mg/kg of body weight per day. In the treatment of adult humans, the range of about 0.06 to about 250 mg/kg, in single or divided doses, is preferred. However, it will be understood that the amount of compound actually administered will be determined by a physician in light of the relevant circumstances, including (1) the condition to be treated, (2) the choice of compound to be administered, (3) the chosen route of administration, (4) the age, weight and response of the individual patient, and (5) the severity of the patient's symptoms. Therefore, the above dosage ranges are not intended to limit the scope of the invention in any way. by "active ingredient" is meant a polyamine as described herein or a salt thereof with a pharmaceutically acceptable acid. By "salt" is meant an addition salt between the polyamine of the invention and a sufficient amount of pharmacologically appropriate acid, such as hydrochloric, sulfuric, phosphoric, acetic, butyric, citric, maleic, lactic, valeric, tartaric, gluconic, succinic and the like, made by conventional chemical means.

What is claimed is:

1. An aminated polyamine having the formula:

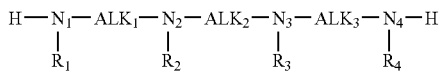

or its possible stereoisomers or a salt thereof with a pharmaceutically acceptable acid wherein:

$R_1$ and $R_4$ may be the same or different and are alkyl, aryl, aryl alkyl or cycloalkyl, optionally having an alkyl chain interrupted by at least one etheric oxygen atom;

$R_2$ and $R_3$ may be the same or different and are $R_1$, $R_4$ or H;

$N_1$, $N_2$, $N_3$ and $N_4$ are nitrogen atoms capable of protonation at physiological pH's;

$ALK_1$, $ALK_2$ AND $ALK_3$ may be the same or different and are straight or branched chain alkylene bridging groups having 1 to 4 carbon atoms which effectively maintain the distance between the nitrogen atoms such that the polyamine:

(i) is capable of uptake by a target cell upon administration of the polyamine to a human or non-human animal or is capable of binding to at least one polyamine site of a receptor located within or on the surface of a cell upon administration of the polyamine to a human or non-human animal; and (ii) upon uptake by the target cell, competitively binds via an electrostatic interaction between the positively charged nitrogen atoms to biological counter-anions; the polyamine, upon binding to the biological counter-anion in the cell, functions in a manner biologically different than the intracellular polyamines; and further wherein at least one of said bridging groups $ALK_1$, $ALK_2$ and $ALK_3$ contains at least one —CH (NRH)— group which is not alpha- to either of the nitrogen atoms and R is H, alkyl, acyl or sulfonyl.

2. A polyamine of claim 1 having the formula:

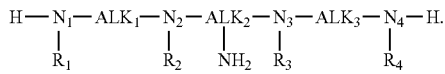

3. A polyamine of claim 1 having the formula:

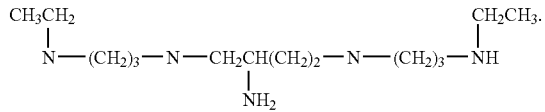

4. A pharmaceutical composition comprising an antineoplastic effective amount of an aminated polyamine of claim 1 or a salt thereof with a pharmaceutically acceptable acid and a pharmaceutically acceptable carrier therefore.

5. A method of treating a neoplasm in a human or non-human animal in need thereof comprising administering thereto an anti-neoplastic effective amount of an aminated polyamine of claim 1 or a salt thereof with a pharmaceutically acceptable acid.

6. An article of manufacture comprising packaging material and a pharmaceutical agent contained within said packaging material, wherein said pharmaceutical agent is effective for the treatment of a subject requiring antineoplastic therapy, and wherein said packaging material comprises a label which indicates that said pharmaceutical agent can be used for antineoplastic therapy, and wherein said pharmaceutical agent is an aminated polyamine of claim 1.

7. A method of increasing uptake of a pharmacore into a cell, comprising covalently attaching a polyamine to the pharmacore, optionally indirectly via a linking group, to form a conjugate having a polyamine moiety, wherein the polyamine moiety comprises the aminated polyamine of claim 1, and contacting the cell with the conjugate or a salt, solvate or hydrate thereof.

8. The method of claim 7 wherein said pharmacore is an antibiotic, antiviral or chelating agent.

9. A vector adapted for the intracellular delivery of a pharmacore comprising a conjugate of a polyamine covalently attached, optionally indirectly attached via a linking group, to a pharmacore, said conjugate having a polyamine moiety, wherein the polyamine moiety comprises the aminated polyamine of claim 1.

10. The Vector of claim 9 wherein said pharmacore is an antibiotic, antiviral or chelating agent.

* * * * *